(12) United States Patent
Greszler

(10) Patent No.: US 6,408,682 B2
(45) Date of Patent: Jun. 25, 2002

(54) LEAK DETECTION METHOD FOR ENDOSCOPES

(75) Inventor: Alan J. Greszler, Elyria, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/813,869

(22) Filed: Mar. 21, 2001

Related U.S. Application Data

(63) Continuation-in-part of application No. 09/498,870, filed on Feb. 7, 2000.
(60) Provisional application No. 60/193,648, filed on Mar. 31, 2000.

(51) Int. Cl.$^7$ .............................. A61L 2/00; B08B 7/04; G01R 31/12; G05D 7/00; G01N 27/00
(52) U.S. Cl. .......................... 73/40; 73/31.04; 73/49.2; 422/33; 422/119; 422/112; 134/22.12; 134/102.2
(58) Field of Search ....................... 73/40, 29.1, 31.04, 73/49.2; 324/71.1; 422/28, 33, 3, 300, 119, 112; 134/22.12, 102.2

(56) References Cited

U.S. PATENT DOCUMENTS

| | | | |
|---|---|---|---|
| 4,527,551 A | 7/1985 | Ishii | 128/4 |
| 4,538,593 A | 9/1985 | Ishii | 128/4 |
| 4,548,197 A | 10/1985 | Kinoshita | 128/4 |
| 4,896,530 A | 1/1990 | Lehmann | 73/49.2 |
| 5,045,051 A * | 9/1991 | Milder et al. | 600/16 |
| 5,059,913 A * | 10/1991 | Nigro et al. | 324/557 |
| 5,065,350 A | 11/1991 | Fedder | 364/571.03 |
| 5,279,799 A | 1/1994 | Moser | 422/292 |
| 5,303,576 A * | 4/1994 | Erdelsky | 73/40 |
| 5,310,524 A | 5/1994 | Campbell et al. | 422/33 |
| 5,317,896 A * | 6/1994 | Sheth et al. | 73/29.01 |
| 5,492,672 A * | 2/1996 | Childers et al. | 422/28 |
| 5,494,530 A | 2/1996 | Graf | 134/18 |
| 5,578,993 A | 11/1996 | Sitabkhan et al. | 340/614 |
| 5,705,737 A | 1/1998 | Liao | 73/49.7 |
| 5,738,824 A | 4/1998 | Pfeifer | 422/3 |
| 5,858,305 A | 1/1999 | Malchesky | 422/98 |
| 5,882,589 A | 3/1999 | Mariotti | 422/98 |
| 6,047,431 A | 4/2000 | Canonica | 15/104.095 |
| 6,057,689 A * | 5/2000 | Saadat | 324/557 |
| 6,068,815 A * | 5/2000 | Oberleitner et al. | 422/28 |

FOREIGN PATENT DOCUMENTS

JP     04102431     4/1992

* cited by examiner

Primary Examiner—Hezron Williams
Assistant Examiner—David J. Wiggins
(74) Attorney, Agent, or Firm—Fay, Sharpe, Fagan, Minnich & McKee, LLP

(57) ABSTRACT

In automated reprocessing system (B), a leak detection system (10) evaluates the integrity of an endoscope (A), having an internal passage (66). The leak detection system includes an interior chamber (42) which is connected to the internal passage by quick connects (18, 20). A source of compressed air (22) pressurizes the chamber and internal passage to a suitable test pressure. A pressure sensor (50) and a temperature sensor (54) detect the pressure and temperature within the chamber and hence in the endoscope passage. Pressure and temperature measurements made over time are used to determine changes in the gas volume, indicative of whether leaks are present in the endoscope. If the endoscope is determined to be free of leaks, the endoscope is washed and microbially decontaminated in the reprocessing system. During the decontamination process, the pressure within the internal passage is maintained in a range at which ingress of fluid is avoided yet the endoscope is not subjected to a potentially damaging pressure.

16 Claims, 8 Drawing Sheets

LEAK DETECTION METHOD FOR ENDOSCOPES

This application is a Continuation-in-Part of U.S. application Ser. No. 09/498,870, filed Feb. 7, 2000 and claims the priority of U.S. Provisional Application Ser. No. 60/193,648, filed Mar. 31, 2000.

BACKGROUND OF THE INVENTION

The present invention relates to a leak detector for lumened instruments. It finds particular application as a leak detector for endoscopes of the watertight type. It will be appreciated, however, that the invention is also applicable to the detection of leaks in other lumened devices.

Endoscopes and other lumened medical instruments are typically subjected to a thorough cleaning and antimicrobial decontamination between each use. During endoscopic procedures, the devices become coated with blood and other protein-rich body fluids. The endoscopes have a watertight structure in which elements that are sensitive to water, detergents, and antimicrobial agents are contained so that it is possible to wash and sterilize the whole body of the endoscope by immersion or spraying in a washing liquid and an antiseptic solution. However, when there are defects in the watertight structure of the sensitive elements, or pinholes and cracks in a sheath of the endoscope's flexible tube, washing and antiseptic solutions can leak into the inside of the water tight portions of the endoscope. This may lead to corrosion of the operating devices, or leakage of the solutions into the bundle of optical fibers, resulting in hindrance of transmission of light. In addition, patients could be harmed if trapped washing or antiseptic liquids later leak from the inside of the endoscope while in use.

To minimize these problems, methods have been developed to detect for leaks in an endoscope. In a conventional leak test procedure, a source of compressed air is attached to the endoscope. The source exhaust port is closed and the endoscope pressurized until a pressure gauge registers that the pressure within it is within a predetermined "pressure hold" range (typically 1140 to 220 mm of mercury). An observation is made to verify that the scope holds this pressure without falling outside the range. Falling outside this range would indicate a gross leak. The endoscope is then totally submerged in a tub of warm water. If the pressure drops, the endoscope is considered leaky and the test discontinued. If the pressure is maintained in the pressure hold range, the operator is instructed to articulate the control handle knobs of the endoscope to flex the distal tip of the endoscope, and visually inspect the device for bubble generation. An inability to maintain pressure during the pressure hold phase, or the generation of a single bubble in a period of one to two minutes is considered to be an endoscope failure. The operator is instructed to discontinue endoscope reprocessing until the device has been inspected and repaired.

The manual leak check procedure is prone to human error, especially with the increasing demand for rapid reprocessing and turnaround of endoscope devices. For example, bubbles may not become evident until two to three minutes into the pressure hold phase. This is well beyond the one to two minutes time frame allotted for the typical leak check. Another problem with the manual leak check procedure is the potential for the operator to leave the endoscope pressurized during subsequent reprocessing. If this occurs, the distal tip will inflate, as the internal pressure increases in the elevated temperature of the processing solution (typically about 50° C.). This can lead to extensive endoscope damage and costly repairs.

Some automated reprocessing systems include a leak check step prior to disinfection of the endoscope. However, changes in ambient temperature can lead to increases in the internal pressure within the endoscope and lead to erroneous assessments. The reprocessing vessel is frequently warm from a prior reprocessing procedure and the internal temperature of the endoscope often rises, as a result, during the leak check.

Even if a leak detection test is conducted at the beginning of a reprocessing cycle, leaks may develop during the cycle which permit the cleaning fluids to enter the sealed portions of the endoscope during the cycle, or subsequently permit blood or other body fluids to enter during reuse of the endoscope in a surgical procedure.

Continuous leak detection during a reprocessing cycle suffers from inaccuracies, in most cases, since the device being reprocessed is typically subjected to varying temperatures and pressures. To have a test which operates under the variations in temperature experienced results in the test being able to measure only large variations in internal pressure due to relatively large leaks. The test, therefore, may not detect small, pin-hole sized leaks. If the test is designed to be sensitive enough to detect these small leaks, there is a high probability that the device would fail a test where no leak was present.

The present invention provides a new and improved leak detection method, which overcomes the above-referenced problems and others.

SUMMARY OF THE INVENTION

In accordance with one aspect of the present invention, a method for reprocessing an endoscope is provided. The method includes supplying a quantity of gas under pressure to an internal passage of the endoscope to pressurize the internal passage. The temperature and pressure of the gas within the internal passage are measured at a first time. After holding the quantity of gas within the internal passage, the temperature and pressure of the gas within the internal passage are measured at a second time. From the measured temperatures and the measured pressures of the gas within the internal passage at the first and second times it is determined whether leakage of the gas from the internal passage has occurred. In response to determining that the endoscope does not have leaks, a decontamination solution is supplied to contact and decontaminate the endoscope. During decontamination, the pressure of the gas within the endoscope is maintained within a range which is above ambient pressure but below a pressure at which damage to the endoscope may occur.

In accordance with another aspect of the present invention, a method of reprocessing endoscopes is provided. The method includes positioning an endoscope in a reprocessing region and connecting a leak detector to the endoscope. A quantity of compressed gas is supplied to an internal passage of the endoscope to pressurize the internal passage. The method further includes electronically calculating whether the endoscope has leaks from changes in the temperature and pressure of the gas with time. A portion, but not all of the gas within the endoscope is released, such that the pressure of the gas is at an above ambient pressure during decontamination. In response to determining that the endoscope does not have leaks, an antimicrobial fluid is supplied to the reprocessing region to contact and decontaminate the endoscope.

In accordance with another aspect of the present invention, an apparatus for processing endoscopes is provided. The apparatus includes a structure which receives an endoscope to be reprocessed, a pressurized gas source, a means for supplying the pressurized gas from the gas source to an internal passage of the endoscope for selectively pressurizing the internal passage and for holding a quantity of gas in the internal passage fixed. A gas temperature and pressure measuring means is provided for repeatedly measuring a temperature and pressure of the fixed quantity of gas in the internal passage. A leakage determining means receives the measured temperatures and pressures and determines, from changes in the measured temperature and pressure, whether the gas in the internal passage is leaking at a rate greater than a predicted acceptable leakage rate. A source of antimicrobial fluid and a means for supply the antimicrobial fluid to the structure and for contacting and decontaminating surfaces of the endoscope with the antimicrobial fluid are provided. The pressurized gas supplying means supplies pressurized gas to the internal passage to maintain the pressure of the gas in the internal passage above an ambient pressure in the structure while the antimicrobial fluid is contacting and decontaminating the surfaces of the endoscope.

In accordance with another aspect of the present invention, an apparatus for reprocessing endoscopes is provided. The apparatus includes a source of compressed gas and a means for releasably connecting the compressed gas source with an internal passage of an endoscope to be reprocessed and for controlling a supply of compressed gas to the internal passage. A temperature measuring means measures a temperature of the gas in the internal passage. A pressure measuring means measures a pressure of the gas in the internal passage. A source of decontamination solution and a decontamination solution supply means are provided for controllably contacting surfaces of the endoscope with the decontamination solution from the decontamination source. A control means is connected with the compressed gas connecting and controlling means, the temperature measuring means, the pressure measuring means, and the decontamination solution supply means for controlling the compressed gas connecting and controlling means to pressurize the internal passage, controlling the temperature and pressure measuring means to measure temperature and pressure of the gas in the internal passage at least twice, determining whether the internal passage has leaks from changes in the measured temperatures and pressures. After determining whether the internal passage has leaks, the control means controls the compressed gas connecting and controlling means to reduce gas pressure in the internal passage to a lower, above ambient pressure. After determining whether the internal passage has leaks, the control means controls the decontaminant solution supply means to contact and decontaminate the endoscope with the decontaminant solution.

One advantage of at least one embodiment of the present invention resides in rapid detection of leaks in an endoscope.

Another advantage of at least one embodiment of the present invention is that it detects for leaks after a reprocessing operation.

Yet another advantage of at least one embodiment of the present invention is that it minimizes the potential for operator errors.

A still further advantage of the present invention is that it inhibits entry of reprocessing fluids into the sealed portions of the endoscope during a reprocessing operation.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
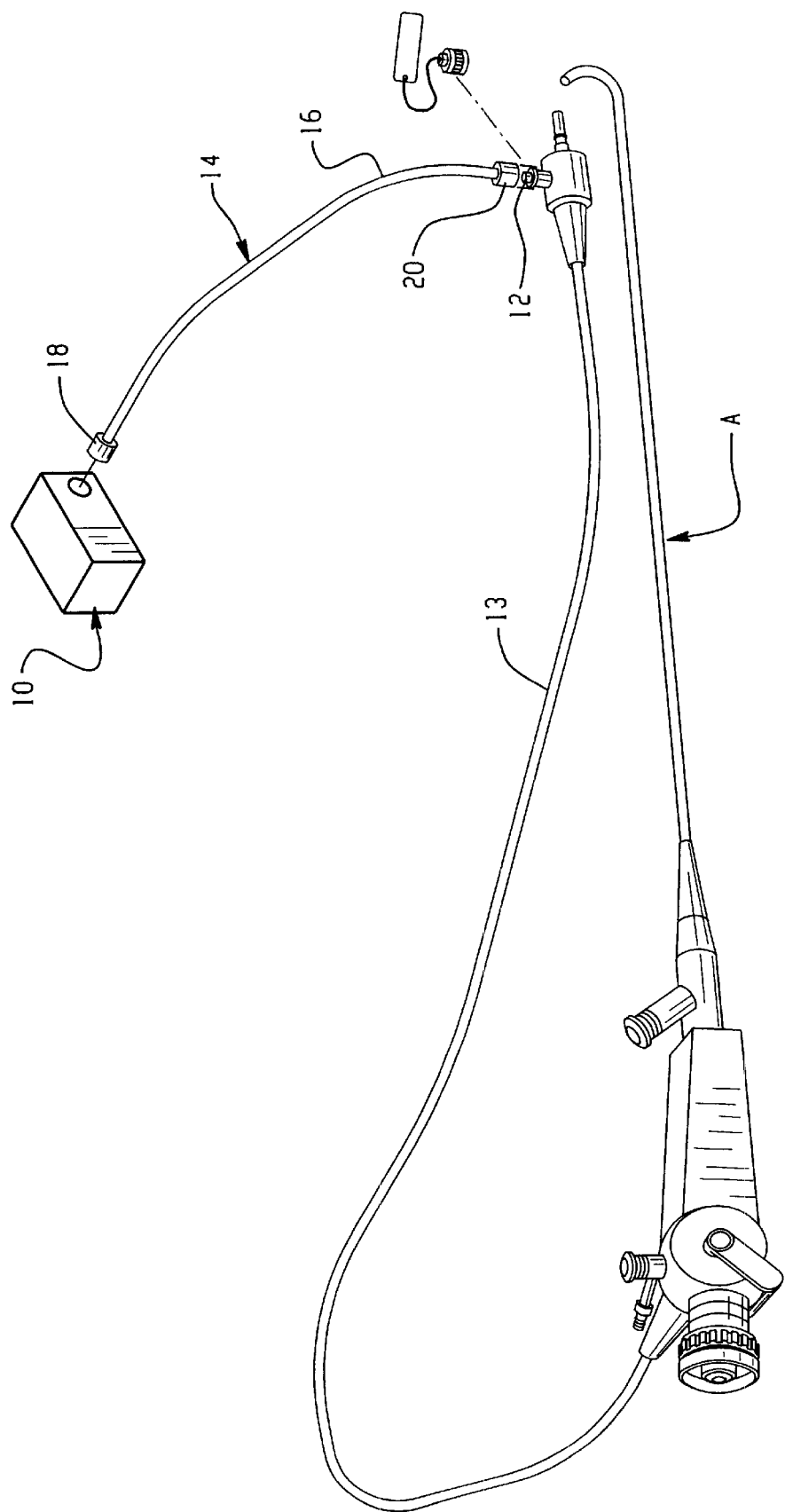
FIG. 1 is a perspective view of a leak detector connected to an endoscope according to the present invention.
Figure 2:
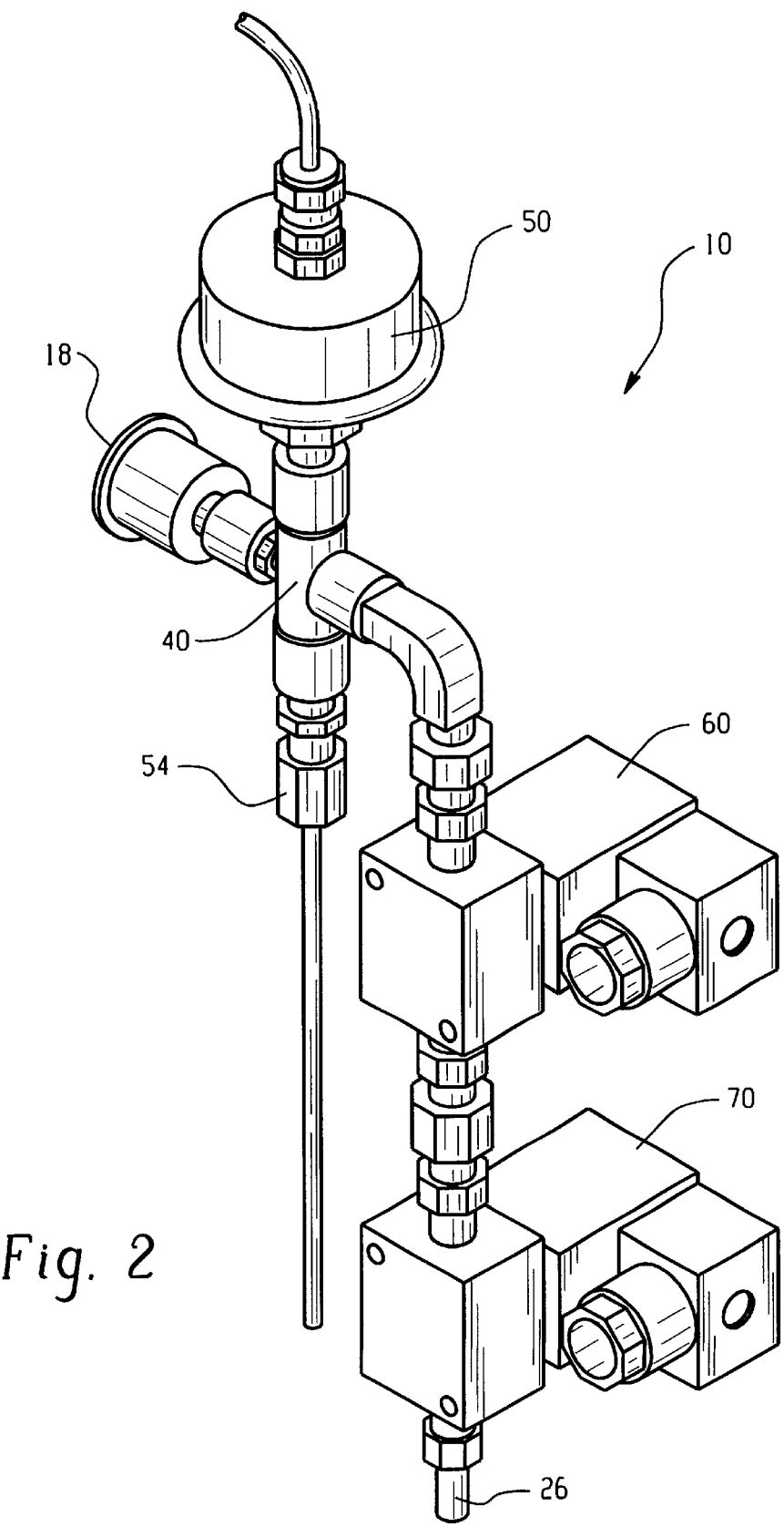
FIG. 2 is a perspective view of the leak detector of FIG. 1.
Figure 3:
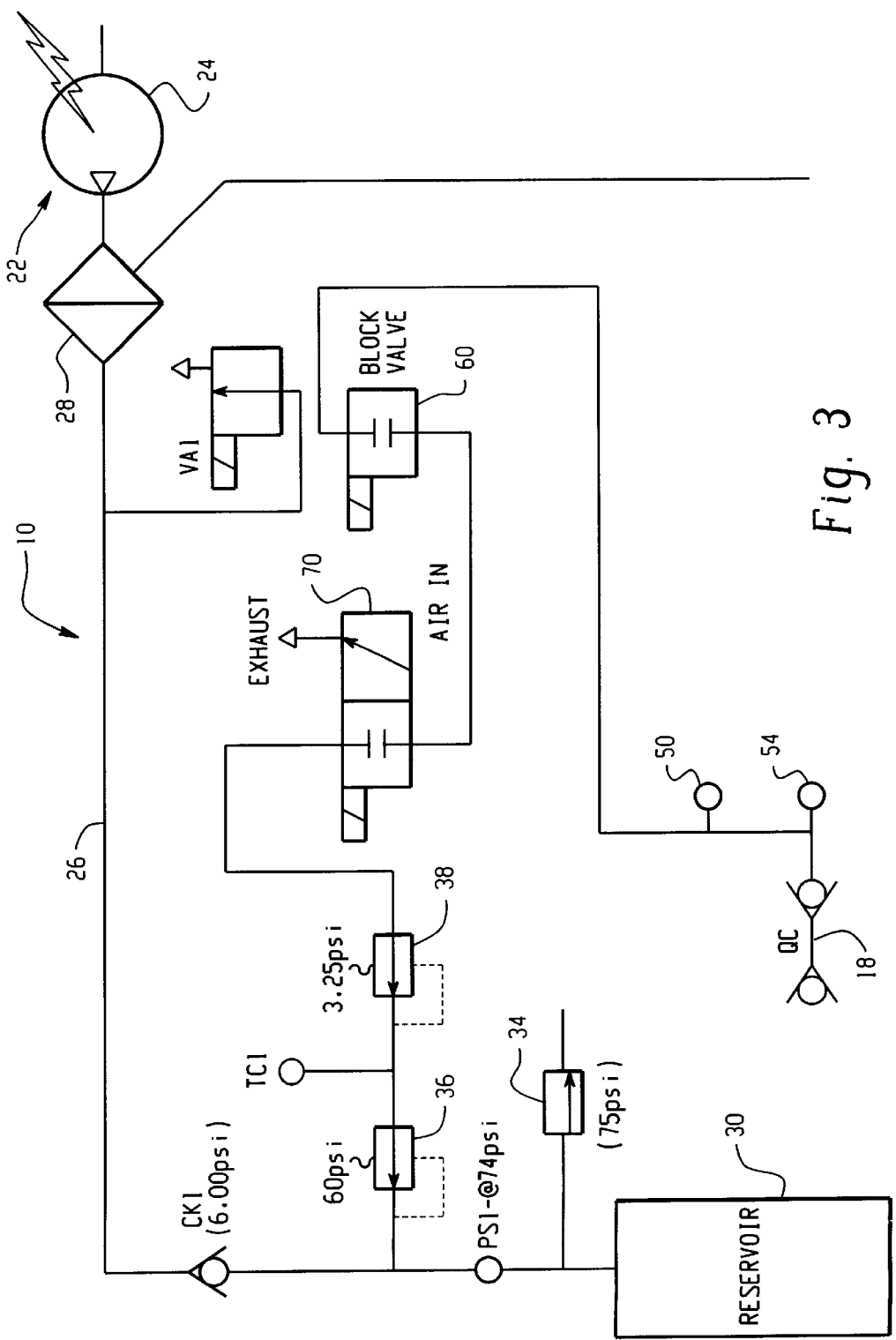
FIG. 3 is a schematic diagram of the leak detector of FIG. 2.

With reference to FIG. 1, a leak detector 10 detects for leaks in an endoscope A or other lumened device before and after a reprocessing operation is carried out and maintains a positive pressure within the endoscope during the reprocessing cycle to inhibit ingress of cleaning and microbial decontaminating fluids into the sealed channels of the endoscope, i.e., those internal passages from which it is desirable to exclude these fluids, such as the umbilical channel of an endoscope. The sealed internal channels carry electronic and optical equipment which may be damaged by contact with the fluids used in a reprocessing cycle.

The leak detector is coupled with a leak test port 12 of an endoscope umbilical cable 13, or other entry port be tested, by a removable connector 14. The connector includes a tubular portion 16, with quick connecting members 18, 20 at opposite ends of the connector. The members 18, 20 are adapted for quickly connecting and disconnecting the connector with the leak detector and the inlet port, respectively, providing a leak tight connection therebetween. The tubing 16 is formed from a material which is relatively rigid and does not tend to stretch when under pressures of about 150–300 mmHg.

With reference now to FIGS. 1 to 4, a source of a compressed gas 22, such as an air compressor or cylinder of pressurized gas 24, supplies compressed air to the leak detector 10 via a fluid line 26. The air is passed through a filter 28 to remove airborne particles. Preferably, the filter 28 (or another desiccating device) also removes moisture from the air.

Optionally, the source of compressed gas also includes a reservoir 30, which is filled from the air compressor prior to a leak test procedure. The leak detector includes one or more pressure regulators 34, 36, 38, which reduce the pressure of the air from the source of compressed gas to a suitable pressure for evaluating the endoscope, typically about 140–190 mmHg. The pressure should be below the maximum rating of the endoscope lumen to be tested but sufficiently high that leaks are apparent during the period of detection.

Figure 4:
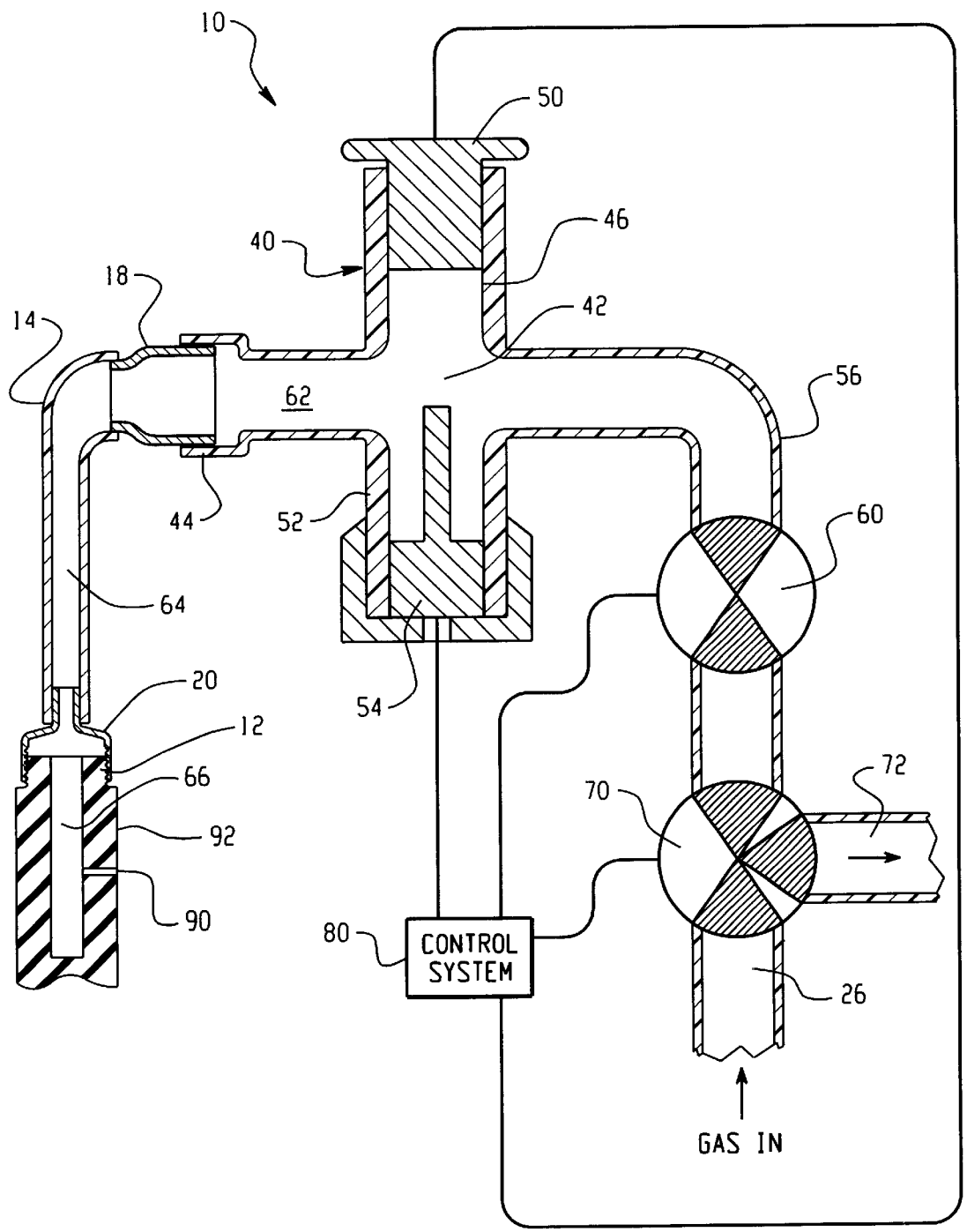
FIG. 4 is a side sectional view of the leak detector of FIG. 2.

With particular reference to FIG. 4, the leak detector 10 includes a cross-shaped tubular member 40 which defines an interior chamber 42 with four connection ports. A first of the connection ports 44 is adapted for connection with the connector quick connect 18. A second inlet port 46 receives a pressure transducer 50, which measures the pressure of the gas within the chamber 42, and, hence, also the pressure within the internal passage of the endoscope. A third inlet port 52 is connected to a temperature detector 54, such as a resistive temperature device, which measures the temperature of the gas within the chamber, and hence also the temperature within the internal passage of the endoscope. A fourth inlet port 56 is connected with the fluid line 26.

A two-way solenoid valve 60 selectively closes the fluid line 26 to seal the fourth inlet port 56. An enclosed space 62 of volume $V_1$ is thus defined, which includes the chamber 42, an internal passage 64 of the connector 14, and the lumen 66 of the endoscope to be evaluated.

A three-way solenoid valve 70 is preferably provided between the two-way solenoid valve 60 and the source 22 of compressed air to allow venting of the space 62, through a vent line 72 before and after leak testing, and to reduce back-pressure on the two-way solenoid valve during leak testing. While the system is described with reference to solenoid valves, other valves may be used. The valves preferably provide a high degree of leak resistance and open and close under automated control accurately and reproducibly.

A control system 80 receives pressure signals from the pressure transducer 50 and temperature signals from the temperature detector 54, and controls the opening and closing of the valves 60 and 70.

To test for leaks, the enclosed space 62 is filled with gas to a set pressure $P_0$. If there are no leaks in the endoscope A, the pressure of gas in the enclosed space, should remain constant over time. However, because the temperature of the gas tends to change over the detection period, the pressure of the gas also tends to change, irrespective of any leaks. Thus, preferably, pressure alone is not used for determining leaks. Accordingly, both temperature and pressure are used to determine whether leakage is occurring. The Ideal Gas Law (1) is used to calculate changes in gas volume during a detection period:

$$V_o = nRT/P \qquad (1),$$

Where
V=volume
n=number of moles of gas
R=universal gas constant
T=absolute temperature (in degrees K)
P=pressure The number of moles n admitted to the enclosed space 62 can be determined from the time taken to reach an initial pressure $P_0$. Then, an initial volume $V_0$ can be calculated from Equation (1).

If there are leaks in the endoscope's internal passage 66, such as pinholes 90 extending through the outer sheath 92 of the endoscope, then the effective volume V of the gas increases. By measuring temperature and pressure at time $t_1$ and a later time $t_2$, such changes in gas volume can be determined using Boyle's Law, Equation (2):

$$\frac{P_1 V_1}{T_1} = \frac{P_2 V_2}{T_2}, \qquad (2)$$

where $P_1$, $V_1$ and $T_1$ are the pressure, volume, and temperature of the gas at time $t_1$, and $P_2$, $V_2$ and $T_2$ are the pressure, volume, and temperature at time $t_2$.

It will be appreciated that the volumes V determined using this equation are not necessarily absolute volumes. Specifically, the leakage of gas from the endoscope which results in a pressure drop, will lead to an increase in calculated volume V (at constant T).

If the change in volume $(V_2 - V_1)$ is above a preselected level, or if the ratio of $V_2/V_1$ is above a preselected value (which avoids the need to determine an initial value of $V_1$), the endoscope is considered to be defective and is examined and repaired prior to further leak testing.

Alternatively, a rate of change in volume is determined:

$$\frac{V_2 - V_1}{t_2 - t_1} \qquad (3)$$

If the rate of change in volume is more than a preselected level (such as greater than 1 cc/minute), the endoscope is considered to be defective.

Figure 5:
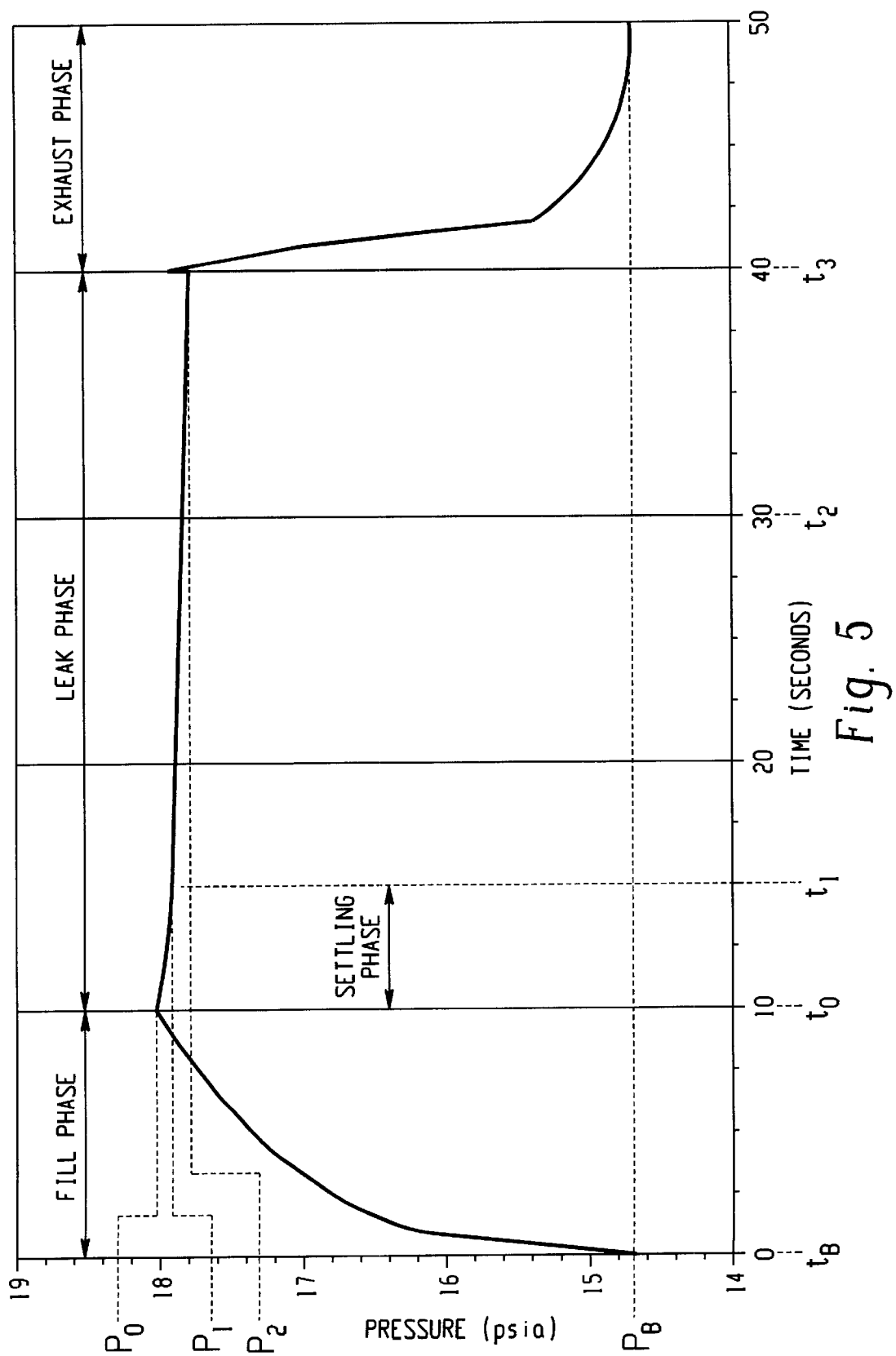
FIG. 5 is a plot of pressure vs time during a leak detection procedure.
Figure 6A:
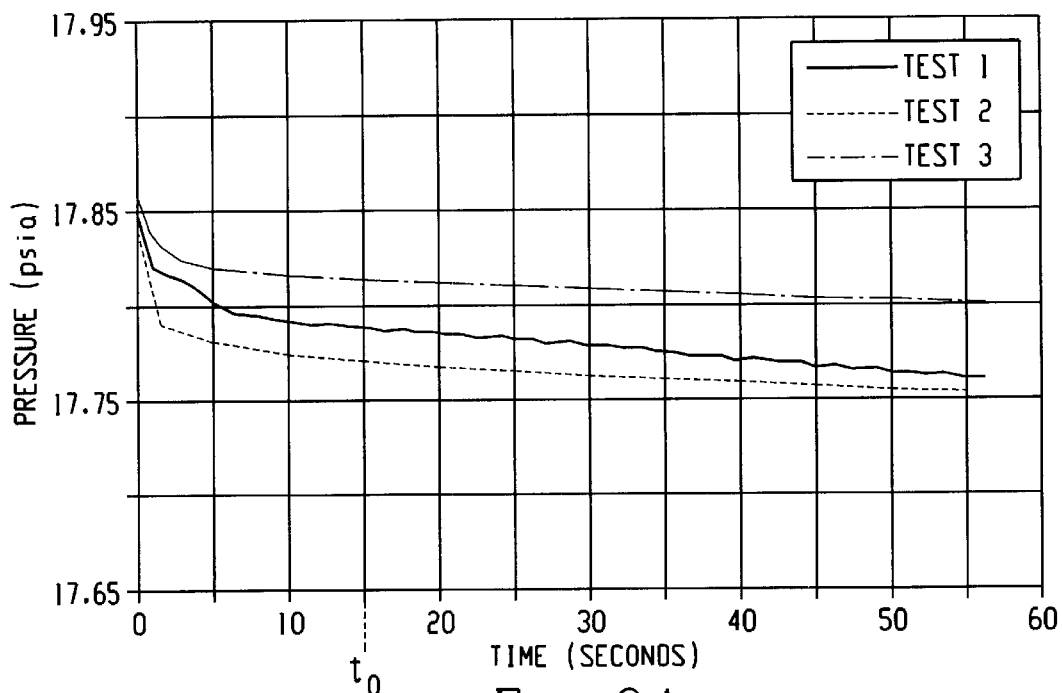
FIG. 6A is a plot of pressure vs time and FIG. 6B is a plot of rate of change in volume vs time for a satisfactory endoscope.
Figure 6B:
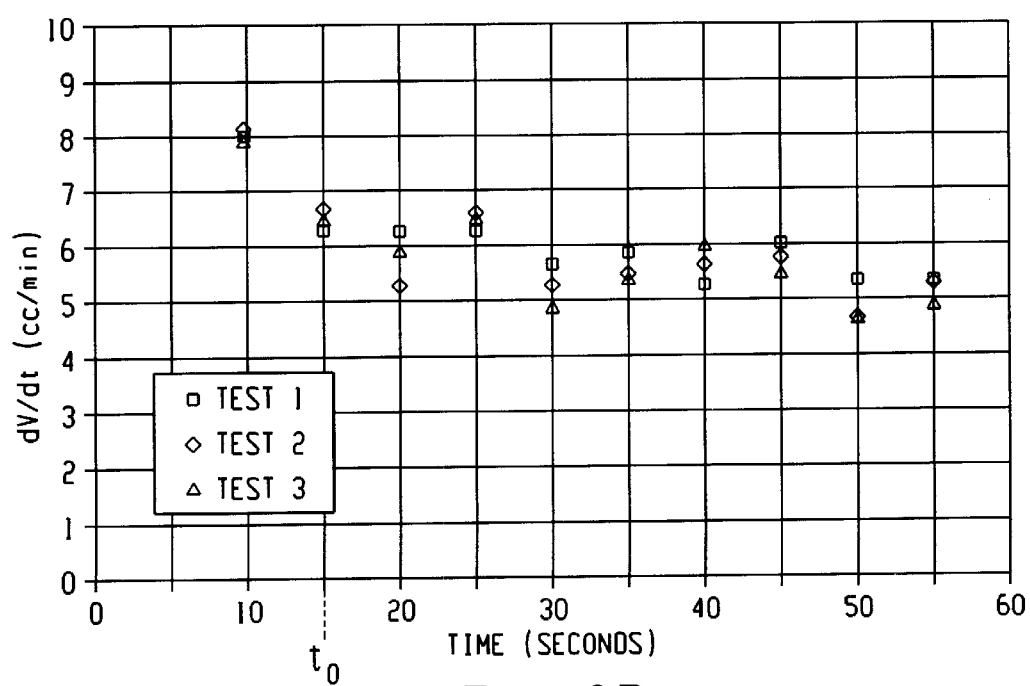

With reference to FIG. 5, the rate of change in volume is preferably calculated for two time periods, namely a first period from $t_1$ to $t_2$, and a second, subsequent period from $t_2$ to $t_3$. If the rate of change is decreasing, this indicates that the endoscope volume may have undergone initial expansion due to stretching of flexible portions under the pressure used.

To perform a leak test, the leak detector 10 is connected with the leak test port of the endoscope A. The control system 80 signals the two way solenoid valve 60 to open, and signals the three-way valve 70 to connect the two-way valve with the vent line 72, thereby venting the enclosed space 62 to the atmosphere.

After a short rest period (about 0.35 seconds), the control system 80 closes the 2-way valve and the baseline values of pressure P and temperature TB are detected by the pressure transducer 50 and temperature detector 54 at time $t_B$.

The 2-way solenoid valve 60 and the 3-way solenoid valve 70 are then both energized by the control system, allowing the endoscope lumen to fill to a preselected destination pressure $P_0$ (the Fill phase). The preselected destination pressure is preferably about 175–190 mmHg(238–258 g/sq.cm) above the baseline pressure $P_B$. If the destination pressure is not reached within a preselected time period, such as 15 seconds, the leak detection cycle is aborted. The failure of the endoscope to reach the destination pressure indicates that either the endoscope A is significantly damaged as it will not hold pressure, or that leak-tight connections between the endoscope and the leak detector 10 have not been properly made. The connections are checked and, if necessary, the damaged endoscope is sent for inspection and repair prior to retesting.

Once the destination pressure $P_0$ is met, the 2-way valve 60 is unpowered to close the valve, sealing the enclosed space 62 at the destination pressure. The time taken to reach the destination pressure $(t_0 - t_B)$ is recorded and can be used to determine the initial volume $V_0$ of gas in the enclosed space 62.

The three way valve 70 is then de-energized to vent pressure between the 2-way and 3-way valves to line 72 to prevent valve seal fluctuation. The pressure and temperature of the air within the endoscope passage are allowed to equilibrate for a settling phase, from $t_0$ to $t_1$, preferably about 5 seconds. At the end of the settling phase, the pressure $P_1$ and temperature $T_1$ are again recorded and can be used to determine $V_1$. If during the settling phase, the endoscope pressure drops to below about 150 mmHg, the cycle is aborted and the endoscope is failed. The settling phase is used to allow for any stretching of the endoscope due to the pressures applied.

A read phase begins at $t_1$, during which time pressure and temperature readings are made at intervals. For example, after a further 15 seconds ($t_2$), readings of temperature $T_2$ and pressure $P_2$ are made. The process is repeated after a further 15 seconds, at time $t_3$. The pressure and temperature readings are used to calculate the effective volumes $V_2$ and $V_3$ of gas corresponding to the temperature and pressure readings at $t_2$ and $t_3$. Using the measurements of volume over time, the control system 80 uses an algorithm to calculate a rate of change in the volume, or other function of pressure and temperature which is indicative of whether there is a leakage of the gas from the enclosed space. If the function measured is outside a preselected range, the control system 80 indicates that further processing is not to be undertaken until the endoscope is examined for damage. For example, if the rate of volume change is in excess of about 1 cc/minute, the endoscope is determined to be defective and is subjected to examination and repair, as appropriate.

The endoscope is subjected to the above described leak detection process before reprocessing (the "pretest leak check") and again after reprocessing (the "postest leak check").

Once the integrity of the endoscope A has been determined in the pretest leak check, the control system 80 signals the 2-way solenoid valve 60 to open and the three-way solenoid valve 70 to vent all or some of the gas to the ambient through vent line 72, removing all or some of the pressure from the endoscope sheath (the Exhaust phase).

With reference to FIGS. 6A, 6B, 7A, and 7B, representative plots of pressure versus time and rate of change in volume with time (dv/dt) are shown for two endoscopes tested for leak using the apparatus of FIGS. 1–4. For improved evaluation of the system, measurements of pressure and temperature were made at 5 second intervals, although, as discussed above, fewer measurements may be made in a leak test check. For each endoscope, the test was repeated three times to assess reproducibility.

The results show good reproducibility of the system. The endoscope of FIGS. 6A and 6B passed the leak detection test. During the read phase from $t_{30}$ to $t_{45}$, the rate of change of volume did not exceed about 1.0 cc/min and the average volume change was less than 1 cc/minute. Moreover, the rate of change of volume approached zero asymptotically over time, suggesting that the endoscope may have undergone some initial stretching in the first few seconds of the test, but was not exhibiting significant change in volume due to leaks.

Figure 7A:
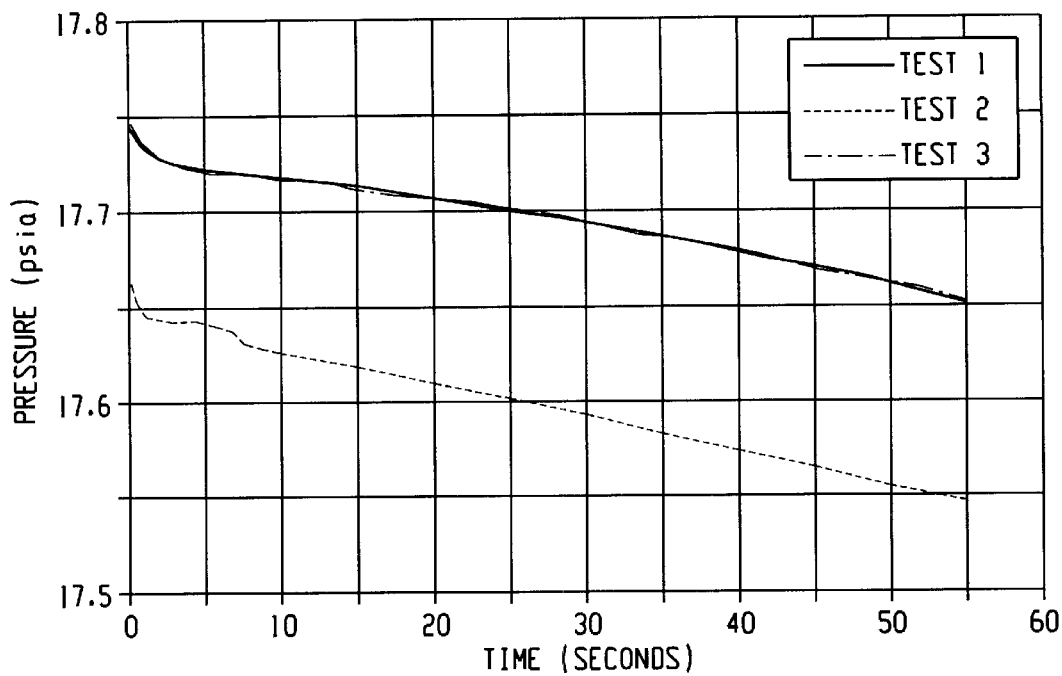
FIG. 7A is a plot of pressure vs time and FIG. 7B is a plot of change in volume vs time for an unsatisfactory endoscope.
Figure 7B:
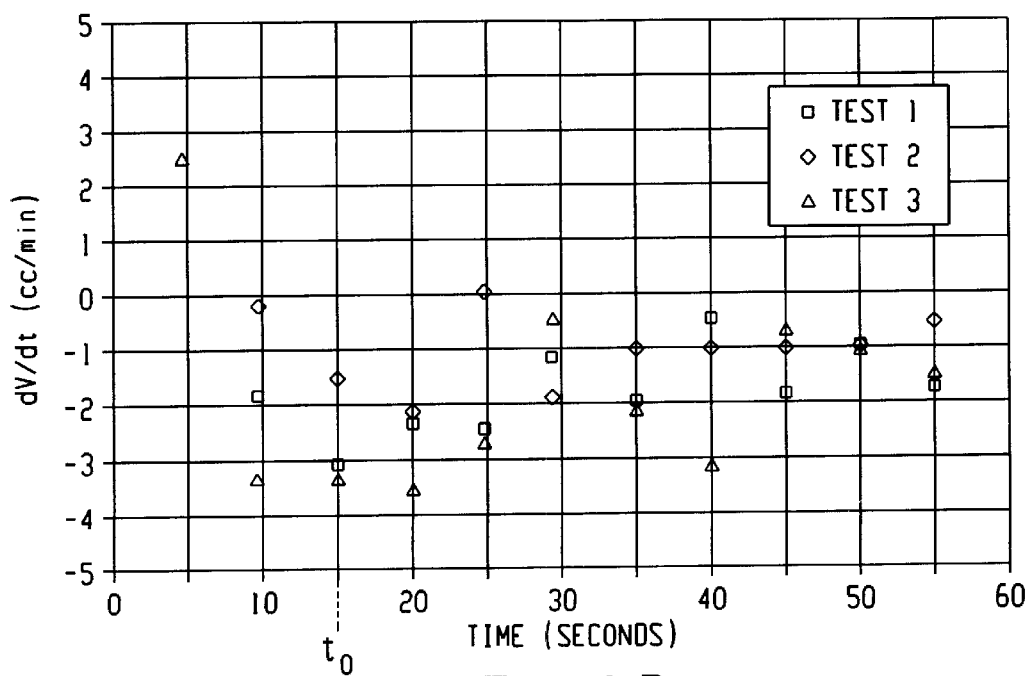

The endoscope represented in FIGS. 7A and 7B failed the test. As shown in FIG. 7A, the pressure continued to drop at a significant rate throughout the test. FIG. 7B shows that the rate of change of volume was, on average, in excess of 3 cc/minute. Additionally, the high rate of loss in volume continued throughout the test period, suggesting the endoscope was defective.

Figure 8:
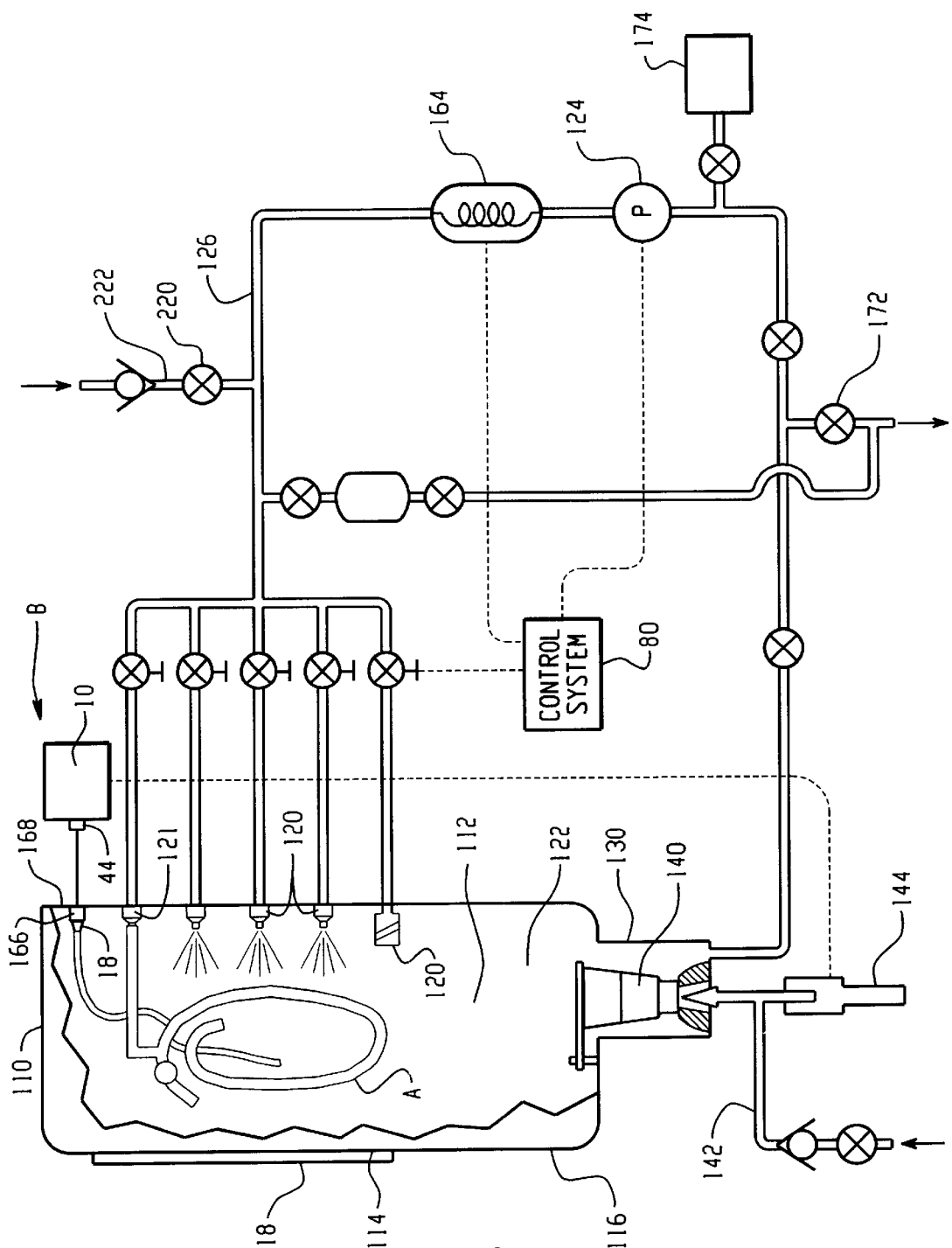
FIG. 8 is a plumbing diagram of an endoscope reprocessing unit incorporating the endoscope leak detector of FIG. 1.

The leak detector 10 can be used to detect for endoscope leaks prior to immersion of the endoscope A in a washing and/or disinfection fluid. Preferably, as shown in FIG. 8, the leak detector is incorporated into an automated washing and microbial decontamination processor B for reprocessing endoscopes.

While particular reference is made to the washing and microbial decontamination of endoscopes, it is to appreciated that the system may also be used to clean and decontaminate a variety of lumened instruments and other devices.

The processor B includes at least one combined washing and microbial decontamination cabinet 110 which defines an interior washing and microbial decontamination chamber 112. Items to be washed and microbially decontaminated are loaded into the chamber 112 through an opening 114 in a vertical front wall 116 of the cabinet closed by a door 118. Within the chamber, jets 120 spray a washing/decontaminant solution over the exterior surface of the endoscopes and other items and connection ports 121 direct the solution through internal passages of the endoscopes and other objects with lumens.

A collection tank or sump 122 forms the base of the cabinet 110 and receives the sprayed washing/decontaminant solution as it drops off the items. A high pressure pump 124 delivers the washing/decontaminate solution under pressure to the spray system through a fluid distribution system 126. A well or mixing chamber 130 sequentially receives doses of a cleaner concentrate and a concentrated decontaminant from separate compartments of a disposable cup 140. The concentrates mix with incoming tap water to form washing and antimicrobial decontamination solutions, respectively.

A preferred antimicrobial agent is peracetic acid, either in concentrated liquid form or as a reaction product of powdered reagents, such as acetyl salicylic acid and sodium perborate. However, it is also contemplated using other liquid or powdered decontaminants or reagents which react in a common solvent to generate peracetic acid, chlorine, hydrogen peroxide, hypochlorous acid, hypochlorite, or other strong oxidants which have biocidal effects. Aldehydes, such as glutaraldehyde, may be used, if care is taken with disposal.

A water inlet line 142 supplies water, typically from a municipal water system, to the well 130. A cup cutter 144, at the base of the well, sequentially opens the compartments. The water mixes with detergents, corrosion inhibitors, the concentrated antimicrobial agent, and other selected components in the cup to form wash, decontaminant, or other solutions. A heater 164 in the fluid supply 126 heats the decontaminant solution to a preferred temperature for effective decontamination.

The control system 80 preferably controls the operation of the processor B, including the pump 124, valves, the cup cutter 144, and the heater 164, in addition to the leak detector 10. A leak testing and reprocessing cycle thus proceeds automatically, from leak testing through final rinsing, without the need for intervention by an operator or transport of the device from one instrument to another.

The leak detector 10 is connected to the endoscope via a connection port 166 in a wall 168 of the chamber 112. The quick connect 18 is connected with the connection port 166, which in turn is connected with the inlet port 44 of the leak detector, housed outside the chamber.

In a typical decontamination cycle, items to be decontaminated are first inserted into the cabinet 110 through the opening 114. The endoscope A to be cleaned is mounted on a rack or other suitable support (not shown) and inserted into the chamber with other items to be cleaned and decontaminated. The fluid connection ports 121 of the chamber are fluidly connected with their respective endoscope inlet ports. The leak detector 10 is connected with the endoscope umbilical port 12, as previously described. A fresh cup 140 is inserted into the well 130 and the chamber closed.

From this point on, the operations of the processor B are automatically controlled by the control system 80. There is no need for an operator to contact the items until all of the steps are complete. A typical cycle includes five phases, namely, a leak testing phase, a washing phase, a microbial decontamination phase, a rinse phase, and a drying phase, which are carried out in sequence. It is contemplated, however, that one or more of these phases may be eliminated, for example, the cycle may proceed directly from the leak testing phase to the microbial decontamination phase without an intermediate washing phase. Or, additional phases may be added to the cycle as appropriate, such as additional rinsing phases.

In the first phase, the control system 80 signals the leak detector 10 to check the endoscope A for leaks. The leak detector goes through the process outlined above.

Preferably, the exhaust phase of the pretest leak detection process does not exhaust all of the gas from the sheath 66 and the leak detectors internal passage 62. This leaves at least a small positive pressure $P_4$ of gas in the endoscope. Or, the endoscope is repressurized with a small amount of gas after the exhaust phase to pressure $P_4$. This pressure $P_4$ is selected to be sufficient to prevent or inhibit ingress of cleaning and or/decontaminating fluids in the subsequent reprocessing of the endoscope, i.e., the pressure $P_5$, achieved during reprocessing, within the endoscope will be above the pressure within the chamber during reprocessing. However, the pressure is not so great as to cause damage to the instrument.

The temperature of the cleaning fluid causes the pressure within the endoscope to rise during reprocessing. The pressure $P_5$ within the endoscope during reprocessing should not exceed the maximum rating $P_6$ set by the manufacturer. Thus, the effects of the temperatures and pressures to be experienced by the endoscope in the chamber 122 during reprocessing are taken into account when determining the pressure of the gas to be retained in the endoscope. The control system 80 signals the two way solenoid valve 60 and the three-way valve 70 to close, sealing the gas within the endoscope. Or, the two way valve 60 may be left open throughout the reprocessing cycle and only the three-way valve 70 closed at this time.

In one embodiment, the passages are sealed 62, 66 throughout reprocessing. In this embodiment, it is contemplated that $P_4$ could be a sub-atmospheric pressure in the endoscope. For example, if it is anticipated that rapid rises in temperature will result in an endoscope internal pressure which is above the external pressure within the chamber once the cleaning and or antimicrobial agents are introduced. The pressure is measured by the pressure transducer and the venting/repressurization is continued until the transducer measures $P_4$.

In a more preferred embodiment, the pressure within the internal passage 66 is monitored by the pressure transducer 50 throughout the reprocessing cycle and is adjusted to maintain $P_5$ at around a preselected level. If the pressure transducer detects a pressure within the endoscope which is above a preselected pressure $P_6$ (which is less than the maximum rating of the endoscope) the control system 80 signals the three-way valve 70 to open to passage 72, venting a portion of the gas from within the endoscope to the surrounding atmosphere. When the pressure detected by the transducer drops to about or below an acceptable level, such as $P_4$, the valve is preferably closed once more, retaining a positive pressure within the endoscope.

If the endoscope pressure drops too low, the three way valve 70 is switched so as to allow compressed gas to enter passages 62, 66 from the reservoir 30 or cylinder 22 of compressed gas until the pressure reaches $P_4$, or some other suitable pressure. Then the valve 70 is closed again to maintain the pressure. In this embodiment, the initial pressure $P_4$, and the maximum pressure $P_5$ are substantially the same, since the venting or addition of gas keeps the endoscope at about $P_4$.

For endoscopes, it is desirable that the pressure during reprocessing $P_5$ (and $P_4$ also if the pressure is to be adjusted during reprocessing) is at least about 0.5 psi (35 g/sq.cm) above the ambient pressure within the chamber 112 to inhibit ingress of fluids into passage 66. Preferably $P_5$ is no more than about 3.25 psi (231 g/sq.cm) above ambient. A suitable pressure for $P_5$ and $P_4$ is about 1 psi (70 g/sq.cm) above ambient. The chamber pressure preferably reaches no more than about 1–3 psi (70–211 g/sq.cm) above atmospheric pressure during reprocessing, thus the endoscope passage 66 is not pressurized to more than about 4–5 psi (281–352 g/sq.cm) above atmospheric pressure. For endoscopes and other devices that are able to withstand higher internal pressures, $P_5$ and $P_4$ may be higher.

Once the endoscope has been pressurized to a desired pressure $P_4$ the washing phase begins. In the washing phase, the items are sprayed and flushed with the washing solution to remove soils, particularly protein, which inhibit access of the decontaminant during the decontamination phase. In the washing phase, the control system signals the opening member 144, to open the cleaner concentrate compartment of the cup 140. The cleaner concentrate mixes with the water to form the washing solution and is delivered by the pump 124 under pressure to the nozzles 120 and the endoscope connection ports 121. A drain valve 172 is then opened to flush the washing solution from the system.

In the decontamination phase, the control system 80 allows more water into the system and signals the heater 164 to heat the water. The microbial decontaminant is then released into the solution. At the end of the decontaminating phase, the valve 172 opens once more to flush the decontaminant solution from the processor to the drain. Finally a sterile rinse water is supplied to the system for rinsing the decontaminated items without risk of recontamination. A source of sterile 174 water supplies the water to the system on demand. Finally, in the drying stage, the control system signals a valve 220 in an air line 222 to open and supply microbe-free air to the system to dry the decontaminated items. The air line is connected with the manifold 126 so that the air flows through the nozzles and connection ports, drying the interior and exterior surfaces of the endoscopes and other items.

At the end of the reprocessing cycle, the posttest leak check is carried out. This may be done with the cabinet closed or open. Even though the endoscope internal channel may be cooling off fairly quickly, the leak detection method compensates for these changes in temperature, allowing an accurate measure of the existence of any leaks. This is a repeat of the pretest leak check. Preferably, the remaining air in the endoscope passage 66 is first exhausted to atmosphere, before the posttest leak check is carried out, by opening valve 70. After the posttest leak check, the endoscope is disconnected from the leak tester.

The dried items are removed from the decontamination chamber 112 for immediate reuse or transferred to sterile pouches and stored until needed.

If the posttest leak check indicates that the endoscope has developed a leak, the endoscope is sent for inspection and repair and then preferably reprocessed again using the above described procedure prior to reuse in a surgical procedure.

While the system B has been described with reference to nozzles which spray the washing and decontaminant solutions over the device A, other ways of contacting the device with the solutions are also contemplated, such as immersion of the device therein. In an immersion system, the endoscope passage 66 is maintained at a pressure which prevents the liquid in which the endoscope is immersed (i.e., the cleaning, antimicrobial, and/or rinse liquids). Thus $P_5$ is greater than the pressure exerted by the liquid, preferably at least about 0.5 psi (35 g/sq.cm) above, and more preferably about 1 psi (70 g/sq.cm) above the liquid pressure.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for reprocessing an endoscope, the method comprising:
   (a) supplying a quantity of gas under pressure to an internal passage of the endoscope to pressurize the internal passage;
   (b) measuring a temperature and a pressure of the gas within the internal passage at a first time;
   (c) holding the quantity of gas within the internal passage;
   (d) after step (c), measuring the temperature and pressure of the gas within the internal passage at a second time;
   (e) determining from the measured temperatures and the measured pressures of the gas within the internal passage at the first and second times whether leakage of the gas from the internal passage has occurred;
   (f) in response to determining that the endoscope does not have leaks, contacting and decontaminating the endoscope with a decontamination solution; and
   (g) during step (f), maintaining the pressure of the gas within the endoscope within a range which is above ambient pressure but below a pressure at which damage to the endoscope may occur.

2. The method of claim 1, wherein the determining step (e) includes:
   determining whether leakage of the gas from the internal passage is at a rate which exceeds a preselected acceptable rate.

3. The method of claim 1, further including, prior to the contacting and decontaminating step (f):
   venting a portion of the gas from the internal passage.

4. The method of claim 1, wherein the pressure maintaining step (g) includes
   detecting the pressure of the gas within the endoscope and carrying out at least one of:
   (h) venting gas from the endoscope in response to detecting pressure above a preselected maximum pressure; and
   (j) adding gas to the endoscope in response to detecting pressure is below a preselected minimum pressure.

5. The method of claim 4, further including:
   repeating steps (h) and (j) at intervals during step (g).

6. The method of claim 1, further including:
   concurrently with step (c), causing the temperature of the interior passage to rise.

7. The method of claim 1, wherein, determining step (e) includes:
   determining whether gas leakage has occurred at less than one cubic centimeter per minute.

8. The method of claim 1, wherein the gas supplying step (a) includes:
   determining whether the pressure in the internal passage reaches a preselected minimum pressure, and
   in response to the internal passage failing to reach the minimum pressure, examining the device for damage prior to commencing step (b).

9. The method of claim 1, wherein the gas supplying step (a) includes:
   measuring a time taken to fill the internal passage to a selected pressure; and
   determining a quantity of gas in the internal passage from the time taken to fill the internal passage to a selected pressure.

10. The method of claim 9, further including:
    comparing the measured fill time with a preselected maximum fill time.

11. The method of claim 1, further including, after the contacting and decontaminating step(f):
    repeating steps (c)–(e).

12. The method of claim 1, wherein the contacting and decontaminating step (f) includes:
    spraying a heated decontaminant solution over the endoscope.

13. A method of reprocessing endoscopes, the method comprising:
    (a) positioning an endoscope in a reprocessing region;
    (b) connecting a leak detector to the endoscope;
    (c) supplying a quantity of compressed gas to an internal passage of the endoscope to pressurize the internal passage;
    (d) electronically calculating whether the endoscope has leaks from changes in the temperature and pressure of the gas with time;
    (e) releasing a portion but not all of the gas within the endoscope such that the pressure of the gas is above ambient pressure during step (f); and
    (f) in response to calculating that the endoscope does not have leaks, supplying an antimicrobial fluid to the reprocessing region to contact and decontaminate the endoscope.

14. The method of claim 13, further including:
    maintaining the pressure within the endoscope at above ambient pressure throughout step (f).

15. An apparatus for processing endoscopes, the apparatus comprising:
    (a) a structure which receives an endoscope to be reprocessed;
    (b) a pressurized gas source;
    (c) a means for supplying the pressurized gas from the gas source to an internal passage of the endoscope for selectively pressurizing the internal passage and for holding a quantity of gas in the internal passage fixed;
    (d) a gas temperature and pressure measuring means for repeatedly measuring a temperature and pressure of the fixed quantity of gas in the internal passage;
    (e) a leakage determining means for receiving the measured temperatures and pressures and determining from changes in the measured temperature and pressure whether the gas in the internal passage is leaking at a rate greater than a predicted acceptable leakage rate;
    (f) a source of antimicrobial fluid;

(g) a means for supply the antimicrobial fluid to the structure and for contacting and decontaminating surfaces of the endoscope with the antimicrobial fluid, the pressurized gas supplying means supplying pressurized gas to the internal passage to maintain the pressure of the gas in the internal passage above an ambient pressure in the structure while the antimicrobial fluid is contacting and decontaminating the surfaces of the endoscope.

16. An apparatus for reprocessing endoscopes, the apparatus comprising:

a source of compressed gas;

a means for releasably connecting the compressed gas source with an internal passage of an endoscope to be reprocessed and for controlling a supply of compressed gas to the internal passage;

a temperature measuring means for measuring a temperature of the gas in the internal passage;

a pressure measuring means for measuring a pressure of the gas in the internal passage;

a source of decontamination solution;

a decontamination solution supply means for controllably contacting surfaces of the endoscope with the decontamination solution from the decontamination source;

a control means connected with the compressed gas connecting and controlling means, the temperature measuring means, the pressure measuring means, and the decontamination solution supply means for:

(a) controlling the compressed gas connecting and controlling means to pressurize the internal passage, (b) controlling the temperature and pressure measuring means to measure temperature and pressure of the gas in the internal passage at least twice, (c) determining whether the internal passage has leaks from changes in the measured temperatures and pressures, (d) after determining whether the internal passage has leaks, controlling the compressed gas connecting and controlling means to reduce gas pressure in the internal passage to a lower, above ambient pressure, (e) after determining whether the internal passage has leaks, controlling the decontaminant solution supply means to contact and decontaminate the endoscope with the decontaminant solution.

* * * * *